(12) United States Patent
Abkowitz et al.

(10) Patent No.: US 8,043,404 B2
(45) Date of Patent: Oct. 25, 2011

(54) HIGH EXTRUSION RATIO TITANIUM METAL MATRIX COMPOSITES

(75) Inventors: Stanley Abkowitz, Lexington, MA (US); Susan M. Abkowitz, Burlington, MA (US); Harvey Fisher, Lexington, MA (US); Patricia J. Schwartz, Andover, MA (US)

(73) Assignee: Dynamet Technology, Inc., Burlington, MA (US)

( * ) Notice: Subject to any disclaimer, the term of this patent is extended or adjusted under 35 U.S.C. 154(b) by 465 days.

(21) Appl. No.: 11/356,025

(22) Filed: Feb. 17, 2006

(65) Prior Publication Data

US 2006/0198755 A1   Sep. 7, 2006

Related U.S. Application Data

(60) Provisional application No. 60/654,475, filed on Feb. 22, 2005.

(51) Int. Cl.
 C22C 49/11 (2006.01)
 C22C 49/12 (2006.01)
 B22F 3/12 (2006.01)
 B22F 3/20 (2006.01)

(52) U.S. Cl. ............... 75/245; 75/236; 75/244; 419/12; 419/14; 419/28; 419/38

(58) Field of Classification Search ............ 75/245, 75/236, 244; 419/28, 12, 14, 38
See application file for complete search history.

(56) References Cited

U.S. PATENT DOCUMENTS

| | | | | |
|---|---|---|---|---|
| 4,852,531 | A * | 8/1989 | Abkowitz et al. | 123/188.3 |
| 5,074,907 | A * | 12/1991 | Amato et al. | 419/19 |
| 5,120,350 | A * | 6/1992 | Supan et al. | 75/232 |
| 5,458,705 | A | 10/1995 | Mazur et al. | |
| 5,854,966 | A * | 12/1998 | Kampe et al. | 419/67 |
| 6,284,014 | B1 * | 9/2001 | Carden | 75/252 |
| 6,399,215 | B1 * | 6/2002 | Zhu et al. | 428/544 |
| 6,551,371 | B1 * | 4/2003 | Furuta et al. | 75/235 |
| 6,599,467 | B1 * | 7/2003 | Yamaguchi et al. | 419/28 |
| 6,635,098 | B2 * | 10/2003 | Abkowitz et al. | 75/245 |
| 2004/0243237 | A1 * | 12/2004 | Unwin et al. | 623/17.11 |
| 2007/0269331 | A1 * | 11/2007 | Moxson et al. | 419/15 |

FOREIGN PATENT DOCUMENTS

WO   WO 99/05332   2/1999

OTHER PUBLICATIONS

Yolton, C.F., The Pre-Alloyed Powder Metallurgy of Titanium with Boron and Carbon Addition, pp. 56-59, Member Journal of the Minerals, Metals and Material Society, May 2004.*
Ma, Z.Y., et al., "In-Situ Ti-TiB Metal-Matrix Composite Prepared by a Reactive Pressing Process," *Scripta mater* 42:367-373 (2000).
Dubey, S., et al., "Fatigue Crack Growth in an In-Situ Titanium Matrix Composite," *Materials Science and Engineering* A266:303-309 (1999).
Dubey, S., et al., "Fatigue Crack Propagation and Fracture Characteristics of In-Situ Titanium-Matrix Composites," *International Journal of Fatigue* 22:161-174 (2000).
Extrusion, $2^{nd}$ ed., Bauser, M. et al. eds., ASM International, pp. 208; 229-239 (2006).
Tool and Manufacturing Engineers Handbook vol. II: Forming, p. 13-24 (1983).

* cited by examiner

*Primary Examiner* — Roy King
*Assistant Examiner* — Ngoclan Mai
(74) *Attorney, Agent, or Firm* — Finnegan, Henderson, Farabow, Garrett & Dunner, LLP

(57) ABSTRACT

Disclosed herein are extruded titanium metal matrix composites with enhanced ductility. Also disclosed is the extrusion at high extrusion ratio of titanium metal matrix composites produced by powder metal processes. The ductility and machinability of these titanium metal matrix composites extruded at high extrusion ratios combined with their wear resistance and excellent imaging characteristics makes these high extrusion ratio extruded titanium metal matrix composites useful as biological implants, including prosthetic devices. Also disclosed are articles such as orthopedic implants for knee, hip, spine or other biomedical devices, with enhanced properties, made from the disclosed extruded material.

13 Claims, No Drawings

HIGH EXTRUSION RATIO TITANIUM METAL MATRIX COMPOSITES

The application claims the benefit of priority to provisional Application No. 60/654,475, filed on Feb. 22, 2005, which is herein incorporated by reference in its entirety.

Disclosed herein are extruded titanium metal matrix composite compositions with enhanced ductility. This invention further discloses orthopedic implant devices for the knee, hip, spine or other prostheses, with enhanced properties than can be fabricated from the disclosed materials and processes. Also disclosed is a process for producing such titanium metal matrix extrusions including a powder metal process for making extrusion billet suitable for subsequent extrusion by the disclosed extrusion process at high extrusion ratio.

Titanium metal matrix composites, especially titanium alloys discontinuously reinforced with additions of titanium carbide (TiC) or titanium diboride ($TiB_2$) or titanium boride (TiB) produced by powder metallurgy, can be used to produce metal-on-metal orthopedic implant devices with significantly improved wear resistance while maintaining the excellent imaging properties of titanium.

For example, titanium carbide/titanium alloy composite and process for powder metal cladding are described in U.S. Pat. No. 4,731,115 to Abkowitz, et al. In addition, titanium diboride/titanium alloy metal matrix microcomposite material and process for powder metal cladding are described in U.S. Pat. No. 4,906,340 to Abkowitz, et al. Also, titanium diboride/titanium alloy metal matrix microcomposite material and process for powder metal cladding are described in U.S. Pat. No. 4,968,348 to Abkowitz, et al. Each of these patents is herein incorporated by reference in its entirety. However, titanium metal matrix composites produced by powder metallurgical processes (involving compaction, sintering and hot pressing) have low tensile ductility that limits their application.

Extrusion, which is defined as the plastic deformation process in which a block (or billet) of metal-based material is forced to flow by compression through a smaller opening than the original billet, can be done hot or cold, depending on the alloy and method employed. Hot extrusion, which involves heating the billet to facilitate plastic deformation, has been used to extrude the above-mentioned materials. This prior work showed that while extrusion increased tensile strength and the ability to fabricate long lengths of these materials the tensile ductility of the resulting material (about 1%) was not significantly improved over that of powder metallurgy (P/M) consolidated materials.

This present disclosure teaches that when powder metal produced composites are extruded at a high extrusion ratio, that is greater then 9 to 1 and such as from 20 to 1, or even 40 to 1, the ductility of the material is increased by about 400% from 1% tensile elongation to 4% tensile elongation. The high extrusion ratio permits manufacture of finished products with higher ductility, facilitates further processing by conventional metal working techniques and also facilitates finish machining of thin sections.

As used herein, "extrusion ratio" is defined by the ratio of the extrusion billet cross sectional area to the cross-sectional area of the resultant extruded product. Thus, if a 3 inch diameter billet is extruded to a ½ inch diameter rod, the extrusion ratio would be calculated as follows:

The cross sectional area of the billet = $(\pi d^2)/4 = (\pi \times 3^2)/4 = 7$;

The cross sectional area of the extrusion = $(\pi d^2)/4 = (\pi \times 0.5^2)/4 = 0.2$; and The extrusion ratio then is = 7 to 0.2 or 35 to 1.

The ductility and machinability of the resulting titanium metal matrix composites combined with their biocompatibility, wear resistance and excellent imaging characteristics makes this material particularly useful as a biomedical implant material including orthopedic devices with articulating wear resistant surfaces such as for knee, hip, shoulder and spine.

Disclosed are powder metal composite materials containing hard ceramic particles in a matrix of titanium alloy produced from a consolidated powder metal billet that is extruded at a high extrusion ratio to produce titanium metal matrix composites with enhanced ductility.

Also disclosed is a wear resistant orthopedic implant device such a hip, knee, shoulder or spinal devices produced from the extruded material by machining or other metalworking methods.

Also disclosed is a process for producing such titanium metal matrix extrusions including a powder metal process for making extrusion billet suitable for subsequent extrusion by the disclosed extrusion process at high extrusion ratio.

For example, there is disclosed an extruded titanium metal matrix composite material having ductility of greater then 3% elongation. In one embodiment, the matrix composite comprises at least one material chosen from alpha, alpha-beta, and beta titanium alloys, and unalloyed Ti.

In one embodiment, the alloys are chosen from Ti-6Al-4V, and Ti-6Al-7Nb. In another embodiment, the material comprises at least one discontinuous reinforcement material chosen from TiC, $TiB_2$, and TiB. The matrix composite may further comprise tungsten (W).

The inventors have found that composite material described herein may be produced by an extrusion process in which the extrusion ratio is greater than 9 to 1, such as an extrusion ratio is greater than 20 to 1.

In one embodiment, there is disclosed an article comprising the disclosed composite material. As stated, the article may comprise an orthopedic device, such as knee, hip, spine and shoulder, implants, and dental implants.

There is also disclosed a powder metallurgy method of making an extruded titanium metal matrix composite material having ductility of greater then 3% elongation.

The method disclosed herein may comprise
blending two or more powders, wherein at least one powder comprises titanium;
compacting the blended powder;
heat treating the compacted and blended powder at a time and temperature sufficient to form a consolidated powder metal; and
extruding the consolidated powder metal at a extrusion ratio greater than 9 to 1.

The example that follows is given as a non-limiting illustration of the present disclosure.

EXAMPLE

A billet of titanium metal matrix composite with composition of Ti-6Al-4V alloy matrix reinforced with 10 wt % TiC particulate dispersed therein was produced by powder metal techniques as generally described in the prior art. This billet was extruded at a high extrusion ratio specifically (25:1 in this case). Table 1 shows typical tensile properties that result from the extrusion at high extrusion ratio of such material, with ductility of the 10% TiC/Ti-6Al-4V metal matrix composite substantially improved. As much as a 5 times improvement in elongation was achieved at essentially equivalent strength levels versus extrusion at low extrusion ratio. Also shown are the results of similar high extrusion ratio of an alternate titanium matrix composition, Ti-6Al-4V with 7.5% tungsten (W) and 7.5% TiC particulate reinforcement produced by the PM method. Again, the properties of this extruded material achieved tensile elongation over 4%.

TABLE 1

| Material Composition | UTS (ksi) | YS (ksi) | Elong (%) | RA (%) |
|---|---|---|---|---|
| 10% TiC/Ti—6Al—4V P/M and Extruded at Low Extrusion Ratio | 155 | 143–6 | 1–2.5 | 4–9 |
| 10% TiC/Ti—6Al—4V P/M and Extruded at High Extrusion Ratio | 155 | 145 | 5 | 9 |
| 7.5% TiC/7.5% W/Ti—6Al—4V P/M Extruded at High Extrusion Ratio | 142 | 126 | 4.6 | 11 |

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

What is claimed is:

1. An extruded titanium metal matrix composite material, said matrix composite comprising a titanium or titanium alloy matrix, tungsten, and at least one discontinuous reinforcing material, wherein said at least one discontinuous reinforcing material comprises ceramic particles selected from the group consisting of TiC, TiB, and TiB$_2$, said ceramic particles having a surface directly in contact with said matrix; and further wherein an extrusion ratio of said matrix composite is greater than 9, and the ductility of said matrix composite is greater than 3% elongation.

2. The material of claim 1, wherein the titanium or titanium alloy matrix comprises at least one material chosen from alpha, alpha-beta, and beta titanium alloys, and unalloyed Ti.

3. The material of claim 2, wherein the alloys are chosen from Ti-6Al-4V, and Ti-6Al-7Nb.

4. The material of claim 1, wherein said extrusion ratio is greater than 20 to 1.

5. An article comprising the material of claim 1, wherein said article is an orthopedic device chosen from knee, hip, spine and shoulder, implants, and dental implants.

6. The article of claim 5, wherein the titanium or titanium alloy matrix comprises at least one material chosen from alpha, alpha-beta, and beta titanium alloys, and unalloyed Ti.

7. The article of claim 6, wherein the alloys are chosen from Ti-6Al-4V, and Ti-6Al-7Nb.

8. An orthopedic device comprising titanium metal matrix composite, said matrix composite comprising a titanium or titanium alloy matrix and at least one discontinuous reinforcing material, wherein said at least one discontinuous reinforcing material comprises ceramic particles selected from the group consisting of TiC, TiB, and TiB$_2$, said particles having a surface directly in contact with said matrix; and said matrix composite is extruded at an extrusion ratio greater than 9 from consolidated powder metal to form an extruded composite, wherein said extruded composite has a ductility of at least 3% elongation.

9. The orthopedic device of claim 8, wherein the titanium or titanium alloy matrix comprises at least one material chosen from alpha, alpha-beta, and beta titanium alloys, and unalloyed Ti.

10. The orthopedic device of claim 9, wherein the alloys are chosen from Ti-6Al-4V, and Ti-6Al-7Nb.

11. The orthopedic device of claim 8, wherein the matrix composite contains W.

12. The orthopedic device of claim 8, wherein the extrusion ratio is greater than 20 to 1.

13. A powder metallurgy method of making an extruded titanium metal matrix composite material having ductility of greater than 3% elongation, said method comprising:

forming a blended powder by blending at least one matrix powder comprising titanium or a titanium alloy with tungsten, and at least one discontinuous reinforcing powder comprising ceramic particles selected from the group consisting of TiC, TiB, and TiB$_2$;

compacting the blended powder;

heat treating the compacted and blended powder at a time and temperature sufficient to form a consolidated powder metal comprising a titanium or titanium alloy matrix, and a discontinuous ceramic reinforcement having a surface in direct contact with said titanium or titanium alloy matrix; and extruding the consolidated powder metal at a extrusion ratio greater than 9 to 1.

* * * * *